(12) United States Patent
Hattori et al.

(10) Patent No.: US 6,238,857 B1
(45) Date of Patent: May 29, 2001

(54) METHOD FOR ANALYZING INTRACELLULAR COMPONENTS

(75) Inventors: Noriaki Hattori; Keiko Yajitate; Motoo Nakajima; Seiji Murakami, all of Chiba (JP)

(73) Assignee: Kikkoman Corporation, Chiba (JP)

( * ) Notice: Subject to any disclaimer, the term of this patent is extended or adjusted under 35 U.S.C. 154(b) by 0 days.

(21) Appl. No.: 09/555,682

(22) PCT Filed: Dec. 1, 1998

(86) PCT No.: PCT/JP98/05407

§ 371 Date: Jun. 2, 2000

§ 102(e) Date: Jun. 2, 2000

(87) PCT Pub. No.: WO99/28495

PCT Pub. Date: Jun. 10, 1999

(30) Foreign Application Priority Data

Dec. 3, 1997 (JP) .................................... 9-347336

(51) Int. Cl.$^7$ ................. C12Q 1/00; C12Q 1/68; C12Q 1/66
(52) U.S. Cl. ........................... 435/4; 435/6; 435/8
(58) Field of Search ................................ 435/4, 6

(56) References Cited

U.S. PATENT DOCUMENTS 5,558,986 * 9/1996 Lundin ..................................... 435/4

FOREIGN PATENT DOCUMENTS

| 63-130139 | 6/1988 | (JP) . |
| 3-251199 | 11/1991 | (JP) . |
| 6-504200 | 5/1994 | (JP) . |
| 7-203995 | 8/1995 | (JP) . |

* cited by examiner

Primary Examiner—Kenneth R. Horlick
Assistant Examiner—Teresa Strzelecka
(74) Attorney, Agent, or Firm—Foley & Lardner

(57) ABSTRACT

A method for analyzing an intracellular component comprising the following steps, and a reagent kit comprising (a) an extraction reagent, (b) branched dextrin or a derivative thereof, and (c) a reagent for analyzing an intracellular component:

(1) step of adding an extraction reagent to a sample containing cells to extract the intracellular component;

(2) step of adding branched dextrin or a derivative thereof to the sample containing the extraction reagent; and (3) step of analyzing the extracted intracellular component.

10 Claims, 4 Drawing Sheets

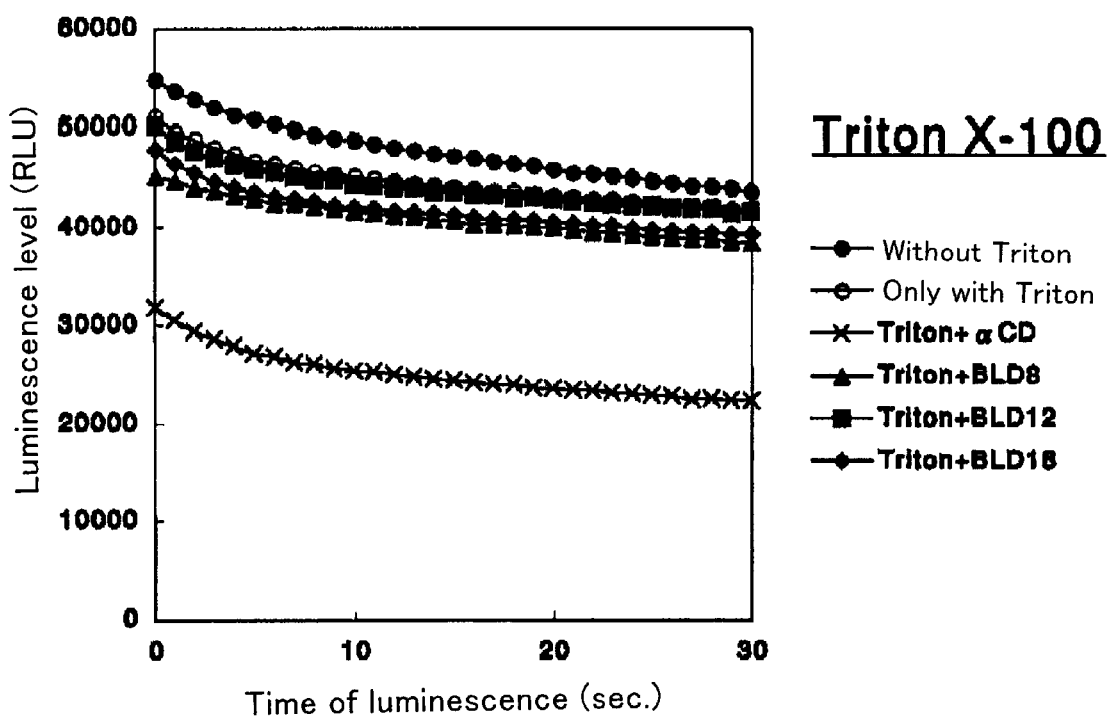

METHOD FOR ANALYZING INTRACELLULAR COMPONENTS

FIELD OF THE INVENTION

The present invention relates to a method and a reagent kit for analyzing an intracellular component.

BACKGROUND OF THE INVENTION

In the fields of food sanitation, biology, clinical test, medical science, ultrapure water and environmental studies, it is common to analyze an intracellular component extracted from cells contained in a sample.

There are various purposes of analyzing the intracellular component, for example, for determining presence/absence, content and activity of the intracellular component, for amplifying nucleic acids, for determining microorganisms in a sample (e.g., determining presence/absence or types of microorganisms, and counting the number of live microbes).

A method for extracting the intracellular component is known in which a reagent for extracting the intracelluar component (hereinafter, referred to as an "extraction reagent") is added to a sample containing cells. Examples of the extraction reagent include ones containing, as an effective component, a detergent, trichloroacetic acid, lytic enzyme such as lysozyme, or ethanol.

Among the above-mentioned extraction reagents, the reagent containing a detergent is frequently used. According to a method that utilizes the extraction reagent containing a detergent as an effective component (hereinafter, referred to as a "detergent method"), examples of the detergent used include anionic detergents (e.g., sodium dodecyl sulfate (SDS), potassium lauryl sulfate, sodium monolauroyl phosphate, sodium alkylbenzenesulfonate), cationic detergents (e.g., benzalkonium chloride (BAC), benzethonium chloride (BZC), cetylpyridinium chloride, cetyltrimethylammonium bromide, myristil dimethylbezyl ammonium chloride), ampholytic detergents (e.g., Twittergent Detergent 3-08, 3-10, 3-12, 3-14, 3-16, Tego) and nonionic detergents (e.g., Tween 20, 60, 80, Span 60, 80, Triton X-45, X-100, polyoxyethylene ether, polyoxyethylene lauryl ether).

According to the detergent method, higher detergent concentration in the extraction reagent results in higher extraction efficiency of the intracellular component. However, higher detergent concentration causes poorer analysis sensitivity and accuracy, as the detergent will inhibit the step of analyzing the intracellular component.

A method for measuring microorganisms is known in which an intracellular component, adenosin triphosphate (ATP), is measured by a bioluminescence method. ATP measurement by the luminescence method is very useful in terms of easiness, short measurement time and high sensitivity. As the bioluminescence method, luciferin-luciferase luminescent reaction method is generally used.

When the detergent is used for extracting ATP in the method for determining the number of cells through luciferin-luciferase luminescent reaction, higher detergent concentration will increase the efficiency of extracting ATP but will also decrease analysis sensitivity and accuracy, as the luminescent reaction is inhibited. This is assumed to be caused by deactivation of enzyme luciferase upon contact with the detergent, which results in rapid decay of luminescence. On the other hand, lower detergent concentration can reduce the inhibition of luminescent reaction but will result in insufficient ATP extraction efficiency.

Intracelluar ATP can be extracted by adding an extraction reagent to a sample containing cells. Usually, the extraction reagent is added such that the final concentration of the detergent is around 0.005%. In order to bring out satisfactory extraction ability, higher final detergent concentration is preferable. However, when the final concentration of the detergent is high (for example, when the final concentration is 0.01% or higher), measurement sensitivity and accuracy are greatly deteriorated as the detergent significantly inhibits the luminescent reaction.

Furthermore, when a nucleic acid is to be amplified by a PCR method, a detergent will inhibit the PCR reaction and no PCR product would appropriately be formed.

When the intracelluar component is an enzyme, there is a problem that the extracted enzyme will be denatured or deactivated by the detergent.

As a substance to repress the interruption of the analysis step (e.g., bioluminescent reaction) caused by the detergent, a method utilizing cyclodextrin or a derivative thereof is known (Japanese National Phase PCT Laid-open Publication No. 6-504200). Another known method for measuring intracellular ATP comprises the steps of: bringing a sample containing cells in contact with a detergent to extract intracellular ATP; and measuring the ATP by luciferin-luciferase luminescent reaction technique, wherein the luminescent reaction technique is applied after bringing the ATP-extracted sample in contact with cyclodextrin (Japanese Laid-Open Publication No. 7-203995).

However, methods utilizing cyclodextrin have the following problems.

(1) Cyclodextrin itself inhibits luminescence: For example, when α-cyclodextrin exists in a luminescent reaction solution at a concentration of 1% or 2%, strong inhibition of 25% or 50% is caused, respectively.

(2) Cyclodextrin is expensive: α-cyclodextrin which has the most superior neutralizing ability of cyclodextrin costs about 20,000 yen per kilogram.

As described above, for a method utilizing an extraction reagent that contains a detergent as an effective component, it is a pressing need to establish a method to efficiently extract an intracellular component without inhibiting the step of analyzing the intracellular component (hereinafter, simply referred to as an "analysis step").

The term "analysis step" as used herein refers literally to a step of analyzing an intracellular component, to a pretreatment for the analysis, and further to any process performed after the step of extracting the intracellular component.

DISCLOSURE OF THE INVENTION

The present inventors have found out that branched dextrin is superior as a substance for repressing the inhibition of the analysis step caused by the extraction reagent (hereinafter, referred to as "neutralizing the extraction reagent" or "neutralization"). The present invention was accomplished based on this finding. Specifically, the present invention is a method for analyzing an intracellular component comprising the steps of: (1) adding an extraction reagent to a sample containing cells to extract the intracellular component; (2) adding branched dextrin or a derivative thereof to the sample containing the extraction reagent; and (3) analyzing the extracted intracellular component.

The present invention is also an analyzing method as described above, wherein the extraction reagent contains a detergent as an effective component.

Furthermore, the present invention is a reagent kit comprising the following constituents: (a) an extraction reagent (stored separately from other components); (b) branched dextrin or a derivative thereof; and (c) a reagent for analyzing an intracellular component.

Hereinafter the present invention will be described in more details.

<Method for Analyzing Intracellular Component>

1. Cell-containing sample

Cells may be derived from animals, plants, microorganisms (for example, yeasts, molds, fungi, bacteria, actinomycetes, unicellular algae, viruses and protozoans) and the like.

A sample is not particularly limited as long as it contains the above-mentioned cell. Examples of such sample include foods, drinks, medicine, cosmetics, seawater, river water, industrial water, sewage, soil, urine, feces, blood, sputum, pus and cultures of the above-mentioned cells. The sample may also be in the form of a solution obtained by suspending any of the above-mentioned sample in an appropriate solvent (e.g., distilled water, physiological saline, phosphate buffer, Tris buffer, sodium acetate buffer). When a specimen contains a solid matter, the specimen is either suspended in an appropriate solvent or homogenized by a mixer or the like so as to be treatable as a solution.

In addition, the above-described solution sample may be filtered through a hydrophilic or hydrophobic filter to capture the cells and use the filter as a sample. When a filter with captured cells is used as a sample, the hydrophilic filter may be, for example, a film or sheet made of hydrophilic polytetrafluoroethylene, hydrophilic polyvinylidene fluoride, hydrophilic polyamide, acetylcellulose, nitrocellulose or the like. The hydrophobic filter may be, for example, one made of PVDF (polyvinylidene fluoride), PTFE (polytetrafluoroethylene), PE (polyethylene) or the like.

2. Extraction of intracellular component

According to the present invention, an extraction reagent is first added to a sample containing cells to extract an intracellular component.

The intracellular component is not particularly limited as long as it is a substance or metabolite contained in the cells. For example, the intracellular component may be a nucleic acid, a protein, a lipid, a vitamin or a polysaccharide. Examples of the nucleic acid include DNA, RNA, ATP, ADP, AMP and cyclic AMP. Examples of the protein include enzymes, hormones and various peptides.

The extraction reagent of the present invention has the following natures.

(1) it functions to extract an intracellular component; and (2) it can be neutralized by branched dextrin or a derivative thereof.

The extraction reagent used for the present invention may be one containing a detergent as an effective component. Examples of the detergent include anionic detergents (e.g., sodium dodecyl sulfate (SDS), potassium lauryl sulfate, sodium monolauroyl phosphate, sodium alkylbenzenesulfonate), cationic detergents (e.g., benzalkonium chloride (BAC), benzethonium chloride (BZC), cetylpyridinium chloride, cetyltrimethylammonium bromide, myristil dimethylbezyl ammonium chloride), ampholytic detergents (e.g., Twittergent Detergent 3-08, 3-10, 3-12, 3-14, 3-16, Tego) and nonionic detergents (e.g., Tween 20, 60, 80, Span 60, 80, Triton X-45, X-100, polyoxyethylene ether, polyoxyethylene lauryl ether).

Conditions for adding the extraction reagent to the sample (i.e., type and concentration of the effective component of the extraction reagent, reaction time and temperature) are not particularly limited, and may appropriately be selected depending on the type of the intracellular component to be analyzed and the conditions of the sample and the cell.

3. Addition of branched dextrin or a derivative thereof

Then, branched dextrin or a derivative thereof (hereinafter, collectively referred to as "branched dextrin") is added to the sample containing the extraction reagent.

The branched dextrin as used herein refers to dextrin containing a branched portion generated upon hydrolyzing starch by an enzymatic (e.g., with amylase) or chemical procedure.

The types, source and molecular weight of the branched dextrin are not particularly limited as long as it is capable of neutralizing the extraction reagent. The branched dextrin may be prepared from starch derived from corn, sweet potato, tapioca, potato or the like, by an enzymatic method using amylase or a chemical method using acid. Amylase that may be used for preparing the branched dextrin may be an endo-type amylase which degrades starch at an arbitrary point or an exo-type amylase which sequentially degrades starch from non-reduced terminal. More specifically, the endo-type amylase may be $\alpha$-amylase, and the exo-type amylase may be exo-1,4-$\alpha$-D-glucosidase, $\beta$-amylase, exo-maltotriohydrolase, exo-maltotetraohydrolase or exo-maltohexaohydrolase. The acid that may be used for preparing the branched dextrin may be an inorganic acid such as hydrochloric acid, or an organic acid such as oxalic acid. The branched dextrin used in the present invention may be prepared by using the above-mentioned amylase and/or acid as a catalyst while treating the starch at an appropriate temperature, pH and for an appropriate reaction time. The branched dextrin prepared by this method contains impurities such as unresolved starch, glucose and low molecular oligosaccharide. The branched dextrin used may contain such impurities. Or, a purified branched dextrin which has been removed of impurities may be used. Also, commercially available branched dextrin may be used. Commercially available branched dextrin that may be used is, for example, BLD8, BLD12, BLD16 (Sanmatsu Kogyo Ltd.), SR-7 (Organo Corp.), Pinedex #100 (Matsutani Chemical Industry Co.,Ltd.) or NSD No.510 (Nihon Shiryo Kogyo K.K.).

Branched dextrin is assumed to exert neutralizing effect by binding to and forming a complex with a detergent. Thus, the amount of the branched dextrin used is preferably in a molar excess of the extraction reagent, considering a stoichiometric amount of the complex to be formed.

The branched dextrin may be dissolved in buffer or water before use.

Conditions for adding the branched dextrin to the sample containing the extraction reagent (i.e., type and concentration of the branched dextrin, reaction time and temperature) are not particularly limited, and may appropriately be selected depending on the type of the extraction reagent to be used, the type of the intracellular component to be analyzed, and the states of the sample and the cell. When the final concentration of the detergent upon the analysis step is about 0.01 to 0.05%, the branched dextrin is added to the final concentration of generally 0.1 to 30%, preferably 1 to 10%.

Addition of the branched dextrin allows the extraction reagent to be neutralized, and the analysis step be carried out with high sensitivity and accuracy.

4. Analysis of the extracted intracellular component

Then, a reagent for analyzing the intracellular component is added to the sample to analyze the extracted intracellular component.

The method and the reagent used for analyzing the intracellular component are not particularly limited as long as the method and the reagent for analysis may be employed for determining the presence/absence, content and activity of the intracellular content, for amplifying a nucleic acid, and for determining microorganisms in a sample (e.g., determining presence/absence or types of microorganisms, determining the number of live microbes).

Such method may be, for example, an enzymatic method, specifically nucleic acid amplification by PCR reaction using DNA polymerase, and determination of intracellular ATP using luciferase.

When the intracellular component is ATP, it is preferably determined by a method based on a bioluminescent luminescent reaction, for example, a luciferin-luciferase luminescent reaction method. The bioluminescence method is very useful in terms of easiness, short measurement time and high sensitivity.

According to the luciferin-luciferase luminescent reaction method, the analysis reagent is added to the sample for luminescence, and the luminescence level thereof is measured. The analysis reagent that may be used is, for example, a bioluminescent reagent containing luciferin, luciferase and magnesium (hereinafter, referred to as a "luciferin-luciferase luminescent reagent").

The luminescence level is measured with a luminometer such as Lumitester K-100 (Kikkoman Corp.), (advanced-type) Luminescence reader BLR-201 (Aloka) and Lumat LB9501 (Berthold). When a filter with captured cells is used as a sample, the number of the cells may be counted by imaging luminescent spots on the filter using a bioluminescent image analysis system device such as ARGUS-50/CL [with tapered fibers: produced by Hamamatsu Photonics K.K.].

The use of luciferin-luciferase luminescent reaction method allows determination of an amount of intracellular ATP, determination of the number of cells in the sample, and the like.

Luciferin and luciferase as used by the invention may be those derived from, for example, insects (such as Luciola cruciata, Luciola lateralis, North American firefly, Russian firefly, *Pynophorus plagiophthalamus* and *Arachnocampa luminosa*). Luciferase may be natural luciferase purified from a luminescent tissue of the above-mentioned organisms, recombinant luciferase prepared by genetic engineering, and mutant luciferase obtained by introducing mutation such as addition, deletion and substitution into one or more amino acids of the amino acid sequence of the natural luciferase.

As the luciferin-luciferase luminescent reagent, a commercially available reagent kit such as "Lucifer LU" (Kikkoman Corp.) may also be used.

According to the present invention, the order of the step of adding the branched dextrin to the sample and the step of analysis is not particularly limited. Therefore, the analysis step may be carried out after the step of adding branched dextrin, or both of the steps may be carried out simultaneously to simplify the procedure. When both steps are carried out simultaneously, a mixed reagent is prepared by adding the branched dextrin to the analysis reagent, and added to the sample containing the extraction reagent.

<Reagent Kit of the Invetion>

A reagent kit of the present invention comprises the following constituents:

(a) an extraction reagent (stored separately from other components);

(b) branched dextrin or a derivative thereof; and (c) a reagent for analyzing the intracellular component.

Of the above-mentioned constituents, constituent (a) is stored separately from other constituents, constituents (b) and (c) may either be separated from each other or mixed together. For the convenience sake, each constituent is preferably dissolved in an appropriate buffer. Furthermore, each constituent may be added with a substance that results in pH adjustment or shelf life improvement of the reagent. Examples of such substance include EDTA2Na, dithiothreitol, ammonium sulfate, sucrose, 2-mercaptoethanol, HEPES, Tricine and Tris. These substances may be added to the reagent kit separately from the above-mentioned constituents (a) to (c).

Constituent (c) may suitably be selected depending on the intracellular component to be analyzed. When intracellular ATP is to be analyzed, constituent (c) may be, for example, a bioluminescent reagent (specifically, luciferin-luciferase luminescent reagent). A commercially available reagent kit, for example, Lucifer LU (Kikkoman Corp.) may also be used as the luminescent reagent.

When the reagent kit of the invention is used, each component may be added to the sample according to the above-described method for analyzing the intracellular component.

BRIEF DESCRIPTION OF THE DRAWINGS

FIG. 7 shows abilities of branched dextrins for neutralizing Triton X-100.

BEST MODES TO CARRY OUT THE INVENTION

Hereinafter, the present invention will be described more specifically by way of examples.

EXAMPLE 1

(Neutralization of Detergent with Various Branched Dextrins)

1. Branched dextrins

Various branched dextrins obtained from various sources were examined for their ability of neutralizing detergents. Twelve kinds of branched dextrins used are listed in Table 1. While BLD 8 is a commercially available product from Sanmatsu Kogyo Ltd., other samples were produced for this test by treating various starch materials listed in the table with amylase. In the table, DE refers to an index representing degradation rate of the starch, where lower DE represents higher viscosity. The various branched dextrins were used after dissolving in 25 mM Tricine (pH 7.75) at a concentration of 10% (w/v). In addition, α-cyclodextrin (αCD, Mercian Corp.) was used as a comparison neutralizing agent.

TABLE 1

| Sample | DE | Source material | Production process |
|---|---|---|---|
| A | 9.3 | Corn | Industrial product |
| B | — | Corn | Hydrogenate an industrial product (no reducing power) |
| C | 6.7 | Corn | Subject an industrial product to weak acid decomposition to decompose large molecular dextrin |
| D | 6.4 | Corn | Act β-amylase on an industrial product to break branched end down to 1–2 in dextrose unit |
| E | 3.6 | Corn | Resolve an industrial product to decrease DE as low as possible |
| F | 5.4 | Sweet potato | Industrially produced from sweet potato |
| G | 6.7 | Sweet potato | Add acid to sweet potato starch and heat the resultant over fire to produce branched dextrin |
| H | 7.5 | Tapioca | Produced from tapioca starch |
| I | 1.1 | corn | β-limit dextrin derived from corn |
| J | 3.7 | potato | β-limit dextrin derived from potato starch |
| K | 11.6 | potato | Add acid to potato starch, heat the resultant over fire, liquefy and resolve with glucoamylase |
| BLD8 | 8.0 | corn | Industrially produced commercial product |

2. Detergent

As a detergent, benzalkonium chloride (BAC, Osban solution according to the Japanese Pharmacopoeia) dissolved in 25 mM Tricine (pH 7.75) at a concentration of 0.1% was used.

3. Determination of ATP

To 100 μl ATP solution ($2 \times 10^{-8}$ M), 50 μl of 0.% BAC and further 50 μl of branched dextrin solution were added. Then, 50 μl of luminescent reagent that comes with "Lucifer LU" (Kikkoman Corp.) was added to measure the generated luminescence level at intervals of 1 sec. for 1 min. using Lumat LB-9501 (Berthold).

4. Results

Figure 1:
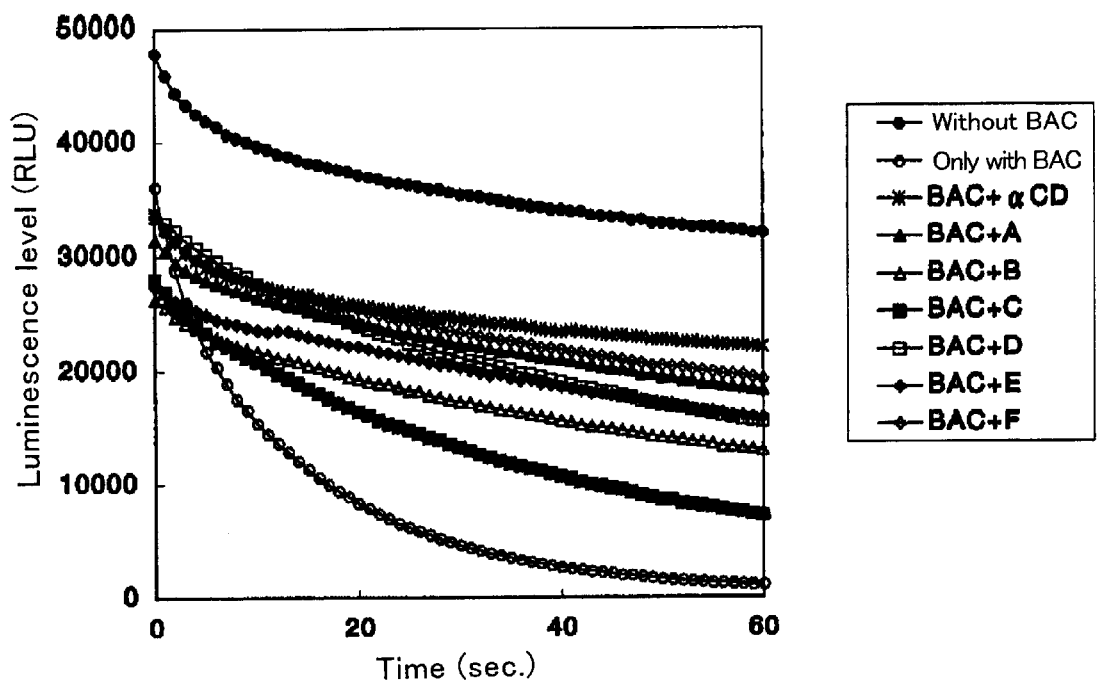
FIG. 1 shows abilities of various branched dextrins for neutralizing luminescent inhibition.
Figure 2:
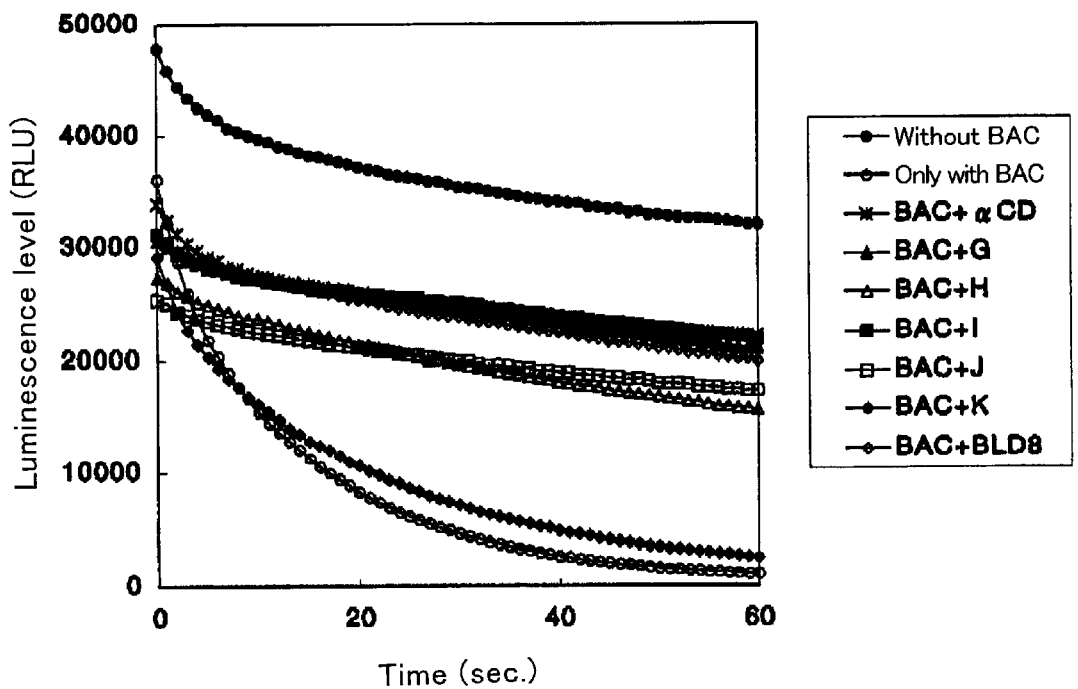
FIG. 2 shows abilities of various branched dextrins for neutralizing luminescent inhibition.

FIGS. 1 and 2 show the results of the determination. "without BAC" represents the case where 25 mM Tricine (pH 7.75) was used instead of 0.1% BAC. "Only BAC" represents the case where 25 mM Tricine (pH 7.75) was used instead of branched dextrin solution. In the figures, the vertical line represents the luminescence level and the horizontal line represents lapsed time after the addition of the bioluminescent reagent.

In the case of "only BAC", luciferase contained in the bioluminescent reagent was deactivated by BAC. As a result, the initial luminescence level was decreased and the luminescence level was rapidly attenuated as compared to the results of the case without BAC. When αCD which is known as a substance for neutralizing a detergent was added, initial luminescence level was reduced while attenuation of luminescence level was greatly decreased. Similar to αCD, the various branched dextrins all decreased attenuation of luminescence. In particular, samples A, D, F, G, I and BLDB showed strong decreasing effect.

Accordingly, similar to αCD, branched dextrins were proved to neutralize deactivation of luciferase caused by a detergent and have an effect of decreasing luminescence inhibition.

EXAMPLE 2
(Inhibition of Bioluminescence Caused by Various Neutralizing Agents Themselves)

Cyclodextrin known as a neutralizing agent for a detergent, itself, exhibits luminescence inhibition and causes deterioration of sensitivity and accuracy. Thus, branched dextrins were tested for bioluminescent inhibition.

1. Branched dextrins used

As branched dextrins, BLD8, BLD12 and BLD16 (all produced by Sanmatsu Kogyo Ltd.) as well as α-cyclodextrin as a comparison (αCD, Mercian Corp.) were used.

2. Determination of ATP

To 100 μl ATP solution ($2 \times 10^{-8}$ M), 50 μl of 25 mM Tricine (pH 7.75) and further 50 μl of 5% and 10% neutralizing solutions (branched dextrins and αCD solution) were added. Then, 50 μl of luminescent reagent that comes with "Lucifer LU" (Kikkoman Corp.) was added to measure the generated luminescence level under the determination conditions of 5 sec. of latency and 3 sec. of integrating time, using Lumat LB-9501 (Berthold).

Together with the determined values, relative percentage of the luminescence level obtained for each neutralizing agent is also shown in Table 2, where the luminescence level obtained without neutralizing agent (i.e., when 25 mM Tricine (pH 7.75) was used instead of neutralizing solution) is 100%.

TABLE 2

| Neutralizing agent | 5% Neutralizing agent (1% upon luminescent reaction) | | 10% Neutralizing agent (2% upon luminescent reaction) | |
|---|---|---|---|---|
| | Determined value (RLU) | Relative percentage (%) | Determined value (RLU) | Relative percentage (%) |
| None | 144336 | (100.0) | 134794 | (100.0) |
| αCD | 108711 | (75.3) | 73392 | (54.4) |
| BLD8 | 140187 | (97.1) | 126318 | (93.7) |
| BLD12 | 140753 | (97.5) | 136503 | (101.3) |
| BLD16 | 143813 | (99.6) | 131229 | (97.4) |

3. Results

αCD exhibited strong luminescent inhibitions of about 25% and 50% upon use of 5% solution (1% concentration at luminescent reaction) and 10% solution (2% concentration at luminescent reaction), respectively. On the other hand, the three branched dextrins exhibited little luminescent inhibition, and the inhibition thereof was only a few % even when 10% solution was used. Accordingly, branched dextrins were proved to induce less luminescence inhibition as compared to αCD which may also be used as a neutralizing agent, and thus advantageous in terms of sensitivity and accuracy in determination.

EXAMPLE 3
(Neutralization of Various Detergents with Branched Dextrins)

Branched dextrins were tested for their abilities to neutralize various detergents.

1. Branched dextrins used

As branched dextrins, BLD8, BLD12 and BLD16 were used. α-cyclodextrin (αCD, Mercian Corp.) was also used as a comparison.

Each of the branched dextrin and αCD was dissolved in 25 mM Tricine (pH 7.75) at 10% (w/v) to be used as a neutralizing solutions.

2. Detergents used

As detergents, benzalkonium chloride (BAC, Osban solution according to the Japanese Pharmacopoeia), benzethonium chloride (BZC, Hyamine solution according to the Japanese Pharmacopoeia), Twittergent 3-16 (Calbiochem), sodium dodecyl sulfate (SDS, Wako Pure Chemical Industries, Ltd.) and Triton X-100 (Wako Pure Chemical Industries, Ltd.) were used. These detergents were each dissolved in 25 mM Tricine (pH 7.75) at a concentration of 0.1% or 0.01% to be used as detergent solutions.

3. Determination of ATP

As described in Example 1, to 100 μl ATP solution ($2\times10^{-8}$ M), 50 μl of detergent and further 50 μl of neutralizing agent were added. Then, 50 μl of luminescent reagent that comes with "Lucifer LU" (Kikkoman Corp.) was added to measure the generated luminescence level at intervals of 1 sec. for 30 sec. using Lumat LB-9501 (Berthold).

Figure 3:
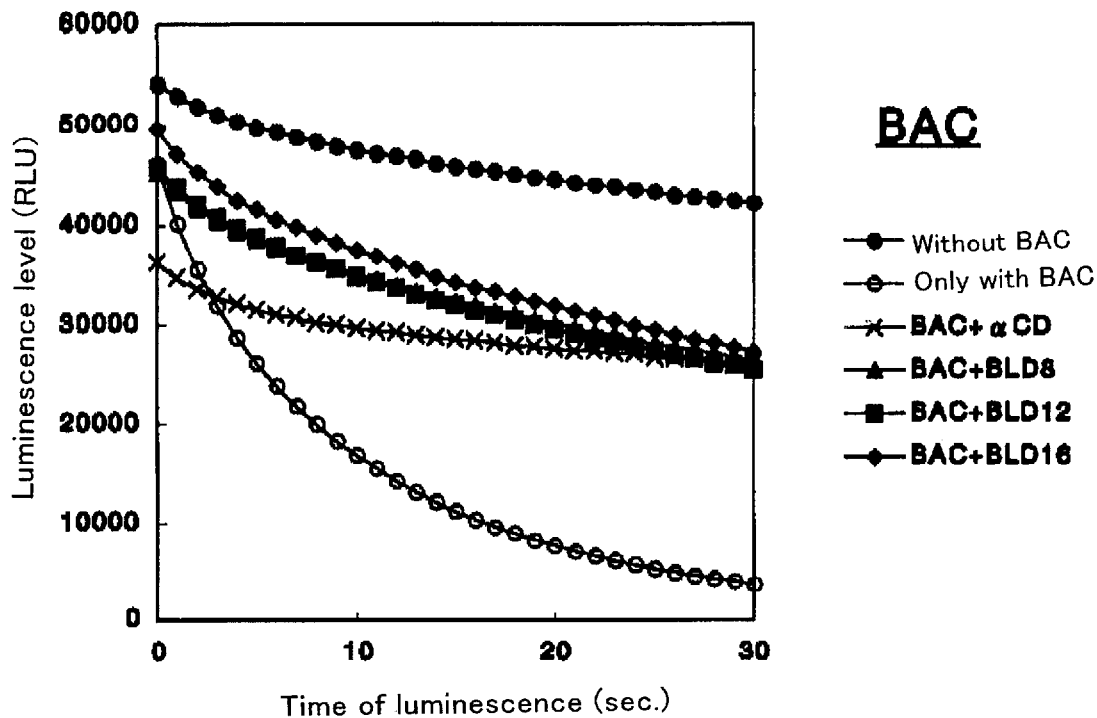
FIG. 3 shows abilities of branched dextrins for neutralizing BAC.

4. Results (1) FIG. 3 shows the results for the case where 0.1% benzalkonium chloride (BAC) was used as a detergent. In the case where only BAC was used, the initial luminescence level was slightly lower than that of the case without BAC, and rapid attenuation of the luminescence level took place. This was considered to be due to deactivation of luciferase in the luminescent reagent caused by BAC.

When αCD was used as a neutralizing agent, attenuation of the luminescence level with the lapse of time was reduced. Similar to αCD, branched dextrins also reduced attenuation of luminescence with the lapse of time. Accordingly, similar to αCD, branched dextrins were proved to exhibit a neutralizing effect for BAC.

Any one of the branched dextrins resulted a higher initial luminescence level than that obtained with αCD, and the luminescence level obtained with the lapse of time was always higher than that obtained with αCD.

For BAC, higher luminescence levels were obtained when the branched dextrins were used as neutralizing agents, proving that the branched dextrins were superior to αCD in neutralizing effect.

Figure 4:
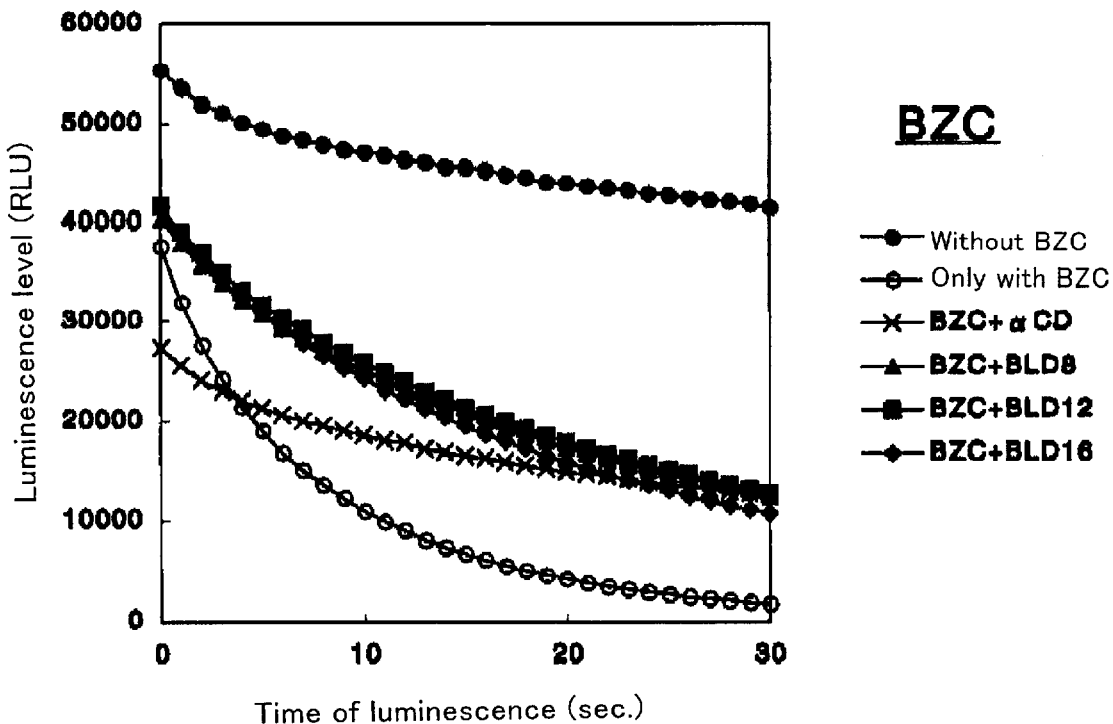
FIG. 4 shows abilities of branched dextrins for neutralizing BZC.

(2) FIG. 4 shows the results for the case where 0.1% benzethonium chloride (BZC) was used as a detergent.

Through the luminescence course in the case where only BZC was used, the initial luminescence level was lower than that obtained without BZC, and the attenuation of luminescence was rapid. When αCD was used as a neutralizing agent, attenuation of the luminescence level with the lapse of time was reduced. Similarly, branched dextrins also reduced attenuation of luminescence with the lapse of time. Accordingly, similar to αCD, branched dextrins were proved to exhibit a neutralizing effect for BZC.

Use of any one of the branched dextrins resulted in a higher initial luminescence level than that obtained with αCD, and the luminescence level obtained with the lapse of time was always higher than that obtained with αCD.

For BZC, higher luminescence levels were obtained when the branched dextrins were used as neutralizing agents, proving that the branched dextrins were superior to αCD in neutralizing effect.

Figure 5:
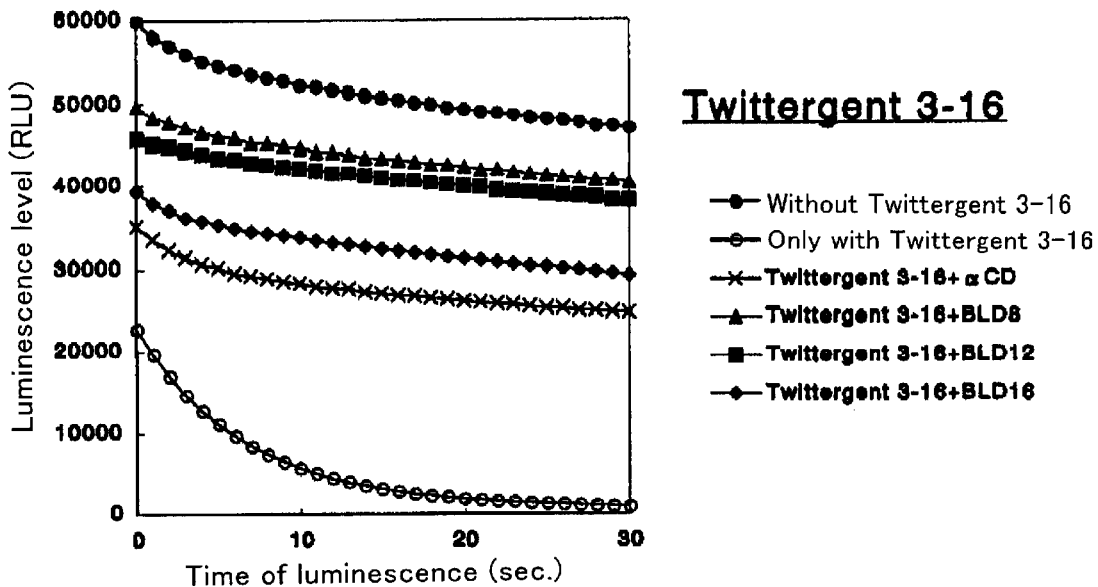
FIG. 5 shows abilities of branched dextrins for neutralizing Twinttergent 3–16.

(3) FIG. 5 shows the results for the case where 0.1% Twittergent 3-16 was used as a detergent. Through the luminescence course in the case where only Twittergent 3-16 was used, the initial luminescence level was as low as one-third the luminescence level obtained with no Twittergent 3-16, and the attenuation of luminescence was rapid. When αCD was used as a neutralizing agent, both the initial luminescence level and the attenuation of the luminescence level were greatly improved. When branched dextrins were used, the initial luminescence level and attenuation of the luminescence level were further improved than with αCD. In particular, BLD8 and BLD12 showed superior neutralizing abilities.

For Twittergent 3-16, higher luminescence levels were obtained when the branched dextrins were used as neutralizing agents, proving that the branched dextrins were superior to αCD in neutralizing effect.

Figure 6:
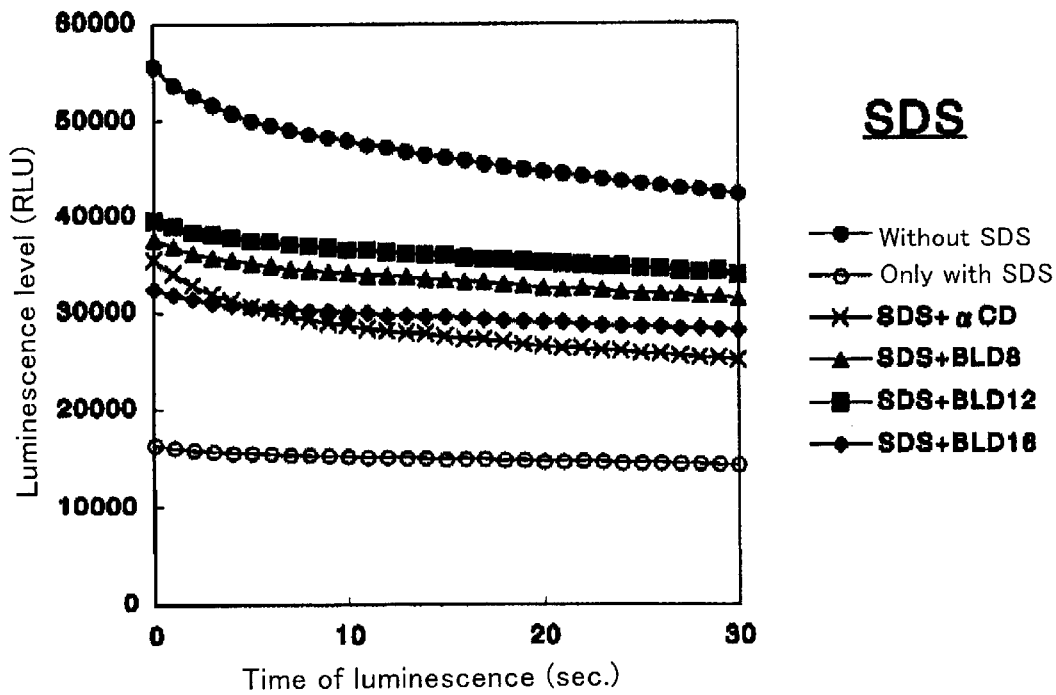
FIG. 6 shows abilities of branched dextrins for neutralizing SDS.

(4) FIG. 6 shows the results for the case where 0.01% sodium dodecyl sulfate (SDS) was used as a detergent. Through the luminescence course in the case where only SDS was used, the luminescence level was significantly lower than that obtained with no SDS. This was due to the inhibition of the luciferase in the bioluminescent reagent as caused by SDS, which reduced the overall luminescence level. When αCD was used as a neutralizing agent, the luminescence level was higher than that obtained with no neutralizing agent. When branched dextrins were used, the luminescence level was high, similar to αCD.

Accordingly, similar to αCD, branched dextrins were proved to exhibit a neutralizing effect for SDS. Higher luminescence levels were obtained particularly when BLD8 and BLD12 were used, and these branched dextrins had higher neutralizing abilities than that of αCD.

(5) FIG. 7 shows the results for the case where 0.01% Triton X-100 was used as a detergent. As for the luminescent transition in the case where only Triton X-100 was used, the luminescence level was slightly lower than that obtained with no Triton X-100, and Triton X-100 did not cause much adverse effect to the luminescent reaction. Where αCD was used as a neutralizing agent, the luminescence level was low due to the luminescent inhibition of αCD itself. On the other hand, when branched dextrins were used, the luminescence levels were the same with or slightly lower than that obtained with no Triton X-100.

For Triton X-100, higher luminescence levels were obtained when the branched dextrins were used as neutralizing agents, proving that the branched dextrins were superior to αCD in neutralizing effect.

EXAMPLE 4

(Determination of Intracellular ATP)

Hereinafter, determination of microorganism intracellular ATP according to the method of the present invention will be described in comparison with determinations according to three conventional methods.

According to Conventional method 1, intracellular ATP was extracted by a TCA extraction method using trichloroacetic acid (TCA), to determine the amount of ATP through luciferin-luciferase reaction. TCA extraction method is very advantageous in terms of ATP extraction efficiency. However, since TCA strongly inhibits luciferin-luciferase reaction, the reaction solution needs to be diluted to a great extent. Accordingly, this method involves complicated procedure, and also has a problem that determination sensitivity may be deteriorated due to the dilution.

According to Conventional method 2, ATP was extracted with a detergent to determine an amount of the extracted ATP through luciferin-luciferase reaction without a neutralizing agent.

According to Conventional method 3, ATP was extracted with a detergent; the action of the detergent was neutralized with cyclodextrin; and an amount of the extracted ATP was determined through luciferin-luciferase reaction (Japanese National Phase PCT Laid-open Publication No. 6-504200, Japanese Laid-open Publication No. 7-203995).

1. Branched dextrin used

BLD8 was used as a branched dextrin. α-cyclodextrin (αCD, Mercian Corp.) was used as a comparison.

2. Detergents used

As detergents, benzalkonium chloride (BAC, Osban solution according to the Japanese Pharmacopoeia) and benzethonium chloride (BZC, Hyamine solution according to the Japanese Pharmacopoeia) were used. Each of these detergents were dissolved in 25 mM Tricine (pH 7.75) at a concentration of 0.1% to be used as a detergent solution.

3. Microorganisms used

As microorganisms, three types of microbes, *Escherichia coli* (ATCC 25922), *Staphylococcus aureus* (ATCC 25923) and *Bacillus subtilis* (ATCC 9372), were used. These microorganisms were cultured overnight in nutrient broth media (Eiken Chemical Co., Ltd.) at 35° C., and the culture solutions were used as determination samples.

According to Conventional method 1, the samples need to be 100-fold diluted before determining the amount of the extracted ATP, in order to avoid inhibition of luminescence by TCA. Accordingly, a raw overnight culture solution was used as a sample in Conventional method 1, and 100-fold diluted solutions thereof were used as samples in other determination methods.

4. Determination of intracellular ATP (1) Present invention

To 100 μl of a sample, 50 μl of a detergent solution was added and left for 20 seconds to extract ATP from the microorganisms. Then, 50 μl of 10% branched dextrin solution and further 50 μl of a bioluminescent reagent were added, and luminescence was measured immediately.

(2) Conventional method 1

To 100 μl of a sample, an equivalent amount of 5% trichloroacetic acid solution was added and left for 1 minute to extract ATP from the microorganisms. To the extracted solution, 9.8 ml of 25 mM Tricine (pH 7.75) was added and well agitated. A hundred μl of this sample was placed into a luminescence measurement tube, to which 100 μl of 25 mM Tricine (pH 7.75) and 100 μl of a luminescent reagent that comes with "Lucifer LU" (Kikkoman Corp.) were added. Immediately after that, luminescence was measured.

(3) Conventional method 2

To 100 μl of a sample, 50 μl of a detergent solution was added and left for 20 seconds to extract ATP from the microorganisms. Then, 50 μl of 25 mM Tricine (pH 7.75) and further 50 μl of a bioluminescent reagent were added, and luminescence was measured immediately.

(4) Conventional method 3

To 100 μl of a sample, 50 μl of a detergent solution was added and left for 20 seconds to extract ATP from the microorganisms. Then, 50 μl of 10% α-cyclodextrin (αCD) solution and further 50 μl of a bioluminescent reagent were added, and luminescence was measured immediately.

5. Results

Table 3 shows the luminescence levels obtained according to the above-described determination methods where benzalkonium chloride (BAC) was used as the detergent. A relative percentage of the luminescence level obtained by each determination method is also shown in the table where the luminescence level obtained according to Conventional method 1 (TCA extraction method) is set as 100%.

TABLE 3

| Determination method | E. coli ATCC 25922 Determined value (RLU) | Relative ratio (%) | S. aureus ATCC 25923 Determined value (RLU) | Relative ratio (%) | B. subtilis ATCC 9372 Determined value (RLU) | Relative ratio (%) |
|---|---|---|---|---|---|---|
| Conventional method 1 (TCA extraction) | 62581 | (100.0) | 133568 | (100.0) | 22262 | (100.0) |
| Conventional method 2 (only with BAC) | 20461 | (32.7) | 42917 | (32.1) | 9445 | (42.4) |

TABLE 3-continued

| Determination method | E. coli ATCC 25922 Determined value (RLU) | Relative ratio (%) | S. aureus ATCC 25923 Determined value (RLU) | Relative ratio (%) | B. subtilis ATCC 9372 Determined value (RLU) | Relative ratio (%) |
|---|---|---|---|---|---|---|
| Conventional method 3 (BAC + αCD) | 31409 | (50.2) | 67623 | (50.6) | 11711 | (52.6) |
| Present invention (BAC + BLD8) | 46934 | (75.0) | 88226 | (66.1) | 16964 | (76.2) |

The luminescence level obtained according to Conventional method 2 (i.e., method using no neutralizing agent) was about 30–40% of that obtained by Conventional method 1 (TCA extraction method), indicating significant luminescence inhibition. The luminescence level obtained according to Conventional method 3 (i.e., method using αCD as a neutralizing agent) was higher than that of Conventional method 2, but was about 50% of that obtained by Conventional method 1 (TCA extraction method).

On the other hand, the luminescence level obtained according to the method of the present invention (i.e., method using branched dextrin as a neutralizing agent) was about 60–80% of that obtained by Conventional method 1 (TCA extraction method), which is approximately twice the luminescence level obtained by Conventional method 2 using no neutralizing agent, showing great improvement in terms of sensitivity and accuracy. The luminescence level obtained by the present invention was higher than that obtained by Conventional method 3 using αCD as a neutralizing agent, which means that the neutralizing ability of the branched dextrin was superior to that of αCD, in determining intracellular ATP of microorganism using BAC.

(2) Table 4 shows the luminescence levels obtained according to the above-described determination methods where benzethonium chloride (BZC) was used as the detergent. A relative percentage of the luminescence level obtained by each determination method is also shown in the table where the luminescence level obtained according to Conventional method 1 (TCA extraction method) is set as 100%.

TABLE 4

| Determination method | E. coli ATCC 25922 Determined value (RLU) | Relative ratio (%) | S. aureus ATCC 25923 Determined value (RLU) | Relative ratio (%) | B. subtilis ATCC 9372 Determined value (RLU) | Relative ratio (%) |
|---|---|---|---|---|---|---|
| Conventional method 1 (TCA extraction) | 67501 | (100.0) | 133568 | (100.0) | 22664 | (100.0) |
| Conventional method 2 (only with BAC) | 19013 | (29.2) | 37936 | (28.4) | 6981 | (30.8) |
| Conventional method 3 (BAC + αCD) | 21544 | (31.9) | 45348 | (34.0) | 8256 | (36.4) |
| Present invention (BAC + BLD8) | 34951 | (51.8) | 73913 | (55.3) | 13795 | (60.9) |

The luminescence level obtained according to Conventional method 2 (i.e., method using no neutralizing agent)

was around 30% of that obtained by Conventional method 1 (TCA extraction method), indicating significant luminescence inhibition similar to the case of BAC. The luminescence level obtained according to Conventional method 3 (i.e., method using αCD as a neutralizing agent) was only slightly higher than that obtained without a neutralizing agent.

On the other hand, the luminescence level obtained according to the method of the present invention (i.e., method using branched dextrin as a neutralizing agent) was about 50–60% of that obtained by Conventional method 1 (TCA extraction method), which is approximately twice the luminescence level obtained by Conventional method 2 using no neutralizing agent, showing great improvement in terms of sensitivity and accuracy. The luminescence level obtained by the present invention was higher than that obtained by Conventional method 3 using αCD as a neutralizing agent, which means that the branched dextrin was proved to be superior as a neutralizing agent to αCD, in determining microorganism ATP using BZC.

Industrial Applicability

Branched dextrins act very well as a substance for suppressing interruption of analysis caused by an extraction reagent. The branched dextrins also have the following advantages.

(1) The branched dextrins have a weak inhibiting activity to bioluminescent reaction as compared to cyclodextrin (when α-cyclodextrin exists in a luminescent reaction solution at a concentration of 1% or 2%, strong inhibition of 25% or 50% is caused, respectively. On the other hand, the branched dextrins show little luminescence inhibition, and inhibits for only a few percents when it exists in a luminescent reaction solution at a concentration of 2%).

(2) The branched dextrins are cost effective (α-cyclodextrin which has the most superior neutralizing ability costs about 20,000 yen per kilogram, whereas the branched dextrins are about 200 yen which is about 1/1000 of the price of the α-cyclodextrin).

The present invention is particularly preferable where an extraction reagent is used which contains a detergent as an effective component. Accordingly, the present invention is preferable as a method for analyzing various intracellular components including intracellular ATP.

What is claimed is:

1. A method for analyzing an intracellular component comprising the steps of:
    (1) adding an extraction reagent to a sample containing cells to extract the intracellular component;
    (2) adding branched dextrin to the sample containing the extraction reagent; and
    (3) analyzing the extracted intracellular component.

2. An analyzing method according to claim 1, wherein the extraction reagent contains a detergent as an effective component.

3. An analyzing method according to claim 1, wherein the intracellular component is any one of nucleic acids, proteins, lipids, vitamins or polysaccharides.

4. An analyzing method according to claim 1, wherein the intracellular component is ATP.

5. An analyzing method according to claim 1, wherein the step of analyzing the extracted intracellular component is performed for the purpose of amplifying nucleic acids, for determining the presence/absence of a microorganism, or for counting the number of live microbes.

6. An analyzing method according to claim 1, wherein the step of analyzing the extracted intracellular component uses an enzyme.

7. An analyzing method according to claim 6, wherein the step that uses an enzyme refers to luciferin-luciferase luminescent reaction method.

8. A reagent kit comprising the following constituents:
    (a) an extraction reagent;
    (b) branched dextrin; and
    (c) a reagent for analyzing an intracellular component.

9. A reagent kit according to claim 8, wherein the extraction reagent contains a detergent as an effective component.

10. A reagent kit according to claim 8, wherein the reagent for analyzing the intracellular component is a luciferin-luciferase bioluminescent reagent.

* * * * *